United States Patent
Laney

(10) Patent No.: US 9,445,980 B2
(45) Date of Patent: *Sep. 20, 2016

(54) METHODS FOR STIMULATING HAIR GROWTH

(76) Inventor: Mark Laney, St. Joseph, MO (US)

(*) Notice: Subject to any disclaimer, the term of this patent is extended or adjusted under 35 U.S.C. 154(b) by 17 days.

This patent is subject to a terminal disclaimer.

(21) Appl. No.: 13/449,581

(22) Filed: Apr. 18, 2012

(65) Prior Publication Data

US 2013/0281369 A1    Oct. 24, 2013

(51) Int. Cl.
| | | |
|---|---|---|
| *A61K 38/18* | (2006.01) | |
| *A61K 38/30* | (2006.01) | |
| *A61K 8/65* | (2006.01) | |
| *A61P 17/14* | (2006.01) | |
| *A61K 8/64* | (2006.01) | |
| *A61Q 7/00* | (2006.01) | |

(52) U.S. Cl.
CPC . *A61K 8/64* (2013.01); *A61K 8/65* (2013.01); *A61K 38/1825* (2013.01); *A61K 38/1841* (2013.01); *A61K 38/1858* (2013.01); *A61K 38/1866* (2013.01); *A61K 38/1875* (2013.01); *A61K 38/30* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 2003/0215412 A1* | 11/2003 | Waugh et al. | 424/70.14 |
| 2005/0208011 A1* | 9/2005 | Marko | 424/70.14 |
| 2006/0239951 A1* | 10/2006 | Valentin et al. | 424/70.14 |
| 2009/0123503 A1* | 5/2009 | Naughton et al. | 424/401 |
| 2010/0129328 A1* | 5/2010 | Sing et al. | 424/93.7 |
| 2012/0116295 A1* | 5/2012 | Isaacs et al. | 604/46 |

OTHER PUBLICATIONS

Shih et al., cancer Letters, 2006, vol. 232(2):139-167.*
Pallua et al., Plast. Reconstr. Surg., 2009, vol. 123(3):826-833.*
Kirsch et al., EMBO J., 2000, vol. 19(13):3314-3324.*

* cited by examiner

*Primary Examiner* — Xiaozhen Xie

(74) *Attorney, Agent, or Firm* — James A. Italia; Italia IP

(57) ABSTRACT

A method for promoting hair growth in a human in need of promoting hair growth. The method includes preparing a composition comprising a therapeutically effective amount of at least three of: a Bone Morphogenetic Protein, Transforming Growth Factor Beta, Platelet Derived Growth Factor, Insulin-like Growth Factor, Basic Fibroblastic Growth Factor and Vascular Endothelial Growth Factor; and administering the composition to the human.

7 Claims, No Drawings

METHODS FOR STIMULATING HAIR GROWTH

BACKGROUND OF INVENTION

The present invention relates to methods of stimulating hair growth, and to pharmaceutical compositions that stimulate hair growth.

SUMMARY

Tens of millions of Americans suffer from some type of hair loss. A wide variety of conditions cause hair loss, including androgenic alopecia, or common pattern baldness, anagen effluvium a chemotherapy-induced hair loss, telogen effluvium, induced by stress, fever and drugs and alopecia areata, an autoimmune disease which afflicts an estimated four million people.

There are two drugs currently approved by the Food & Drug Administration (FDA) for the treatment of male pattern baldness: Rogaine (topical minoxidil) and Propecia (oral finasteride). Both were initially used to treat other medical conditions. Minoxidil, a potassium channel agonist that potently induces peripheral vasodilation, was originally used as a treatment for hypertension. The mechanism by which minoxidil induces hair growth is unknown. Finasteride was originally used to treat urinary problems caused by enlargement of the prostate in men (called benign prostatic hyperplasia). It blocks the activity of 5-alpha-reductase, an enzyme that converts testosterone to dihydrotestosterone (DHT), a more active form of the hormone which has been implicated in miniaturization of hairs, a precursor to catagen.

Minoxidil and finasteride both stimulate hair regrowth in some patients, but only for the duration of drug use: new hair growth ends and hair loss resumes shortly after the patient stops treatment. After several months' use, minoxidil successfully induces limited hair growth for approximately 1 in 3 patients, and slows hair loss for roughly 9 in 10. Oral finasteride is generally more effective than topical minoxidil at inducing hair growth, but both treatments are far less than 100% effective. Further hair loss is prevented in most patients treated with finasteride. About half of treated patients achieve some hair regrowth, and approximately one-third of patients experience cosmetically important hair regrowth after two years of continuous use. Therefore, there exists a significant need for improved compositions and methods for promoting hair growth.

In one embodiment, a method for promoting hair growth in a human in need of promoting hair growth, comprising the steps of: preparing a composition comprising a therapeutically effective amount of at least three of: a Bone Morphogenetic Protein, Transforming Growth Factor Beta, Platelet Derived Growth Factor, Insulin-like Growth Factor, Basic Fibroblastic Growth Factor and Vascular Endothelial Growth Factor; and administering the composition to the human.

In another embodiment, a method for promoting hair growth in a human in need of promoting hair growth, comprising the steps of: preparing a composition comprising a therapeutically effective amount of Ostinol; and administering the composition to the human.

DETAILED DESCRIPTION

According to the present disclosure, methods and compositions for treating humans suffering from hair loss are provided. Some compositions of the present disclosure are prepared by mixing active agent(s) with a variety of pharmaceutically acceptable carriers and/or optional excipients to form a liquid, gel, foam, or cream for topical (e.g., transdermal) application. Other compositions of the present disclosure may be prepared by mixing at least three active agents with a variety of pharmaceutically acceptable carriers and optional excipients to form a liquid, gel or solid for administration by localized injection.

In one embodiment, a composition for the treatment of hair loss by promoting hair growth includes one or more of a Bone Morphogenetic Protein, Transforming Growth Factor-Beta, Platelet Derived Growth Factor, Insulin-like Growth Factor, Basic Fibroblastic Growth Factor and Vascular Endothelial Growth Factor.

As used herein, the terms "Bone Morphogenetic Protein" or "BMP" refer to any mammalian gene, RNA, or protein of the BMP family of TGF-Beta proteins, including, but not limited to, BMPs 2-18 and MP52/GDF-5. In particular, a BMP will have an identifying pattern of seven conserved cysteine residues in the mature, carboxy-terminal portion of the protein, as described in Rosen et al., "Bone Morphogenetic Proteins" Principles of Bone Biology 2:919-928 (2002); and Wozney, J. M., "Bone morphogenetic proteins and their gene expression," CELLULAR AND MOLECULAR BIOLOGY OF BONE 131-167 (Noda, M. ed. 1993). These terms also refer to variants, allelic variants, fragments of, and mutant BMPs, including but not limited to deletion mutants, insertion mutants, and substitution mutants sharing at least 90%, 91%, 92%, 93%, 94%, 95%, 96%, 97%, 98% and 99% amino acid sequence identity with a full-length BMP, or having conservative substitutions at 10%, 9%, 8%, 7%, 6%, 5%, 4%, 3%, 2%, and 1% of amino acid residues, excluding the seven conserved cysteine residues, that retain BMP activity. In Nature Genetics, Oct. 12, 2008, volume 40 pages 1279-1281 a new baldness gene is identified at 20p11.22. The gene locus for BMP2 is Chromosome 20p12. It is believed the proximity indicates that the baldness gene adversely effects the production of BMP2. Thus, BMP2 may provide an important clinical effect in hair regrowth of affected individuals. In the illustrative embodiment, the BMP content of a composition within the scope of the present disclosure may have a percentage by weight between about 35% and about 70% of the composition.

As used herein, the terms "Transforming Growth Factor-Beta" or "TGF-Beta" refer to a superfamily of structurally-related growth factors. This family-of related growth factors is well-known in the art. Kingsley et al., "The TGF-.beta. superfamily: new members, new receptors, and new genetic tests of function in different organisms," Genes Dev. 8:133-146 (1994); Hoodless et al., "Mechanism and function of signaling by the TGF-.beta. superfamily," Curr. Topics Microbiol. Immunol. 228:235-272 (1998). The TGF-Beta superfamily includes bone morphogenetic proteins (BMPs), activin, inhibin, mullerian-inhibiting substance, glial-derived neurotrophic factor, and a still growing number of growth and differentiation factors (GDFs), such as GDF-8 (myostatin). Piek et al., "Specificity, diversity, and regulation in TGF-.beta. superfamily signaling," FASEB J. 13:2105-2124 (1999). In the illustrative embodiment, the TGF-Beta content of a composition within the scope of the present disclosure may have a percentage by weight between about 2.5% and about 10% of the composition.

As used herein, the terms "Platelet Derived Growth Factor" or "PDGF" refer to at least one of the numerous growth factors that regulate growth and division. PDGF is a dimeric glycoprotein composed of two A (-AA) or two B (-BB) chains or a combination of the two (-AB). Hannink, M. "Structure and function of platelet-derived growth factor and related proteins", Biochim. Biophys. Acta. 989 (1): 1-10. There are five different isoforms of PDGF that activate cellular responses through two different receptors. Known ligands include A, B, C, D and an AB heterodimer. PDGF's are mitogenic and drive the proliferation of undifferentiated mesenchyme and some progenitor populations. Other growth factors in this family are vascular endothelial growth factors B and C. Joukov V, "Vascular Endothelial growth factor B, a novel growth factor for endothelial cells". Proc. National Acad. Science USA 93 (6): 2567-2581. PDGF was one of the first growth factors characterized and has led to an understanding of the mechanism of many growth factor signaling pathways. In Cell, Sep. 2, 2011 author Valerie Horsley reports finding MET cells that produce platelet derived growth factors that are necessary to promote hair growth. In the illustrative embodiment, the PDGF content of a composition within the scope of the present disclosure may have a percentage by weight between about 20% and about 40% of the composition.

As used herein, the terms "Insulin-like Growth Factor" or "IGF" are proteins with high sequence similarity to insulin. IGFs are part of a complex system that cells use to communicate with their physiologic environment. This complex system consists of two cell surface receptors (IGF1R and IGF2R), two ligands (IGF-1 and IGF-2) and a family of six high affinity IGF binding proteins (IGFBP1-6). IGFs have been shown to promote cell proliferation and inhibit cell death. IGF-1 consists of 70 amino acids in a single chain with three intramolecular disulfide bridges. It is now widely accepted that signaling through the IGF-1 pathway is a significant contribution to the aging process. Rinderknecht E, "The amino acid sequence of human insulin like growth factor 1 and its structural homology with proinsulin." J Biol. Chem 1978, 253 (2769-76). Rotwein, P "Structure, evolution, expression, and regulation of insulin like growth factors 1 and 2". Growth Factors 1991, 5 (3-18). In the illustrative embodiment, the IGF content, IGF-1 and/or IGF-2, of a composition within the scope of the present disclosure may have a percentage by weight between about 2.5% and about 10% of the composition.

As used herein, the terms "Basic Fibroblastic Growth Factors" or "FGF" refer to a family of growth factors that are key players in the proliferation and differentiation of a wide variety of cells and tissues. In humans there are 22 members of the FGF family that have been identified, all of which are structurally related signaling molecules. FGF2 is also known as Basic Fibroblastic Growth Factor. FGF2 occurs in low molecular weight and high molecular weight isoforms. LMW FGF2 is primarily cytoplasmic and functions in an autocrine manner, whereas HMW FGF2s are nuclear and exert activities through an itracrine mechanism. FGFs are multifunctional proteins with a wide variety of effects; they are most commonly mitogens but also have regulatory, morphological, and endocrine effects. Arese M, "Nuclear activities of basic fibroblastic growth factor: potenitiation of low serum growth mediated by natural or chimeric nuclear localization signals. " Mol. Biol. Cell 10 (5): 1429 44. In the illustrative embodiment, the FGF content, FGF1 and/or FGF2, of a composition within the scope of the present disclosure may have a percentage by weight between about 2.5% and about 10% of the composition.

As used herein, the terms "Vascular Endothelial Growth Factor" or VEGF refer to a sub family of growth factors, such as a platelet derived growth factor family. They are important signaling proteins involved in vasculogenesis and angiogenesis. The broad terms cover a number of proteins from two families that result from alternate splicing of mRNA from a single, 8 exon, VEGF gene. All members of the VEGF family stimulate cellular responses by binding to tyrosine kinase receptors on the cell surface. Ferrara N "The role of vascular endolthelial growth factor in angiogenesis" Acta Haematol 106 (4) 148-56. In the illustrative embodiment, the VEGF content of a composition within the scope of the present disclosure may have a percentage by weight between about 2.5% and about 10% of the composition.

Any suitable carrier may be employed and remain within the scope of the present disclosure. Suitable carriers may include, without limitation, water, an alcohol, minoxidil (e.g. 2%, 5%, etc.), or any other suitable carrier. As used herein, "alcohol" refers to any suitable organic compound in which a hydroxyl functional group is bound to a carbon atom. Illustrative, non-limiting examples of suitable alcohols include isopropyl alcohol, isopropyl myristate, propylene glycol, ethanol, benzyl alcohol, or any other alcohol suitable as a carrier. Other suitable carriers will be apparent to those skilled in the art and are considered within the scope of the present disclosure, and it will be appreciated that the present disclosure is not limited to any of the aforementioned carriers. Further, it will be appreciated that the carrier may be comprised of more than one suitable carrier ingredient as well as any other suitable additive (e.g., moisturizer, etc.). Also, it will be appreciated that any suitable shampoo or conditioner may be employed as a carrier.

In use, the composition is applied to the scalp of the human being treated. The composition may be applied at least once per day, preferably at least twice per day. However, it will be appreciated that the number of applications may vary based on the response. Additionally, it will be appreciated that the course of treatment may last as long as desired and/or needed.

In another embodiment, a composition for promoting hair growth includes topically applying Ostinol™ to a human. Ostinol™ is a nutritional supplement marketed and sold by ZyCal Bioceuticals Inc. Ostinol™ is a complex of proteins naturally found in bones and joints which are functionally involved in the formation of bone and cartilage. Ostinol™ includes partially hydrolyzed collagen and its associated proteins including Bone Morphogenetic Proteins (BMPs). Ostinol™ also includes Transforming Growth Factor-Beta, Platelet Derived Growth Factor, Insulin-like Growth Factor, Basic Fibroblastic Growth Factor and Vascular Endothelial Growth Factor. In the illustrative embodiment, the Ostinol™ content of a composition within the scope of the present disclosure may have a percentage by weight between about 2% and about 20% of the composition.

The composition may include any suitable carrier as previously discussed. In one illustrative embodiment, 150 mg of Ostinol™ is mixed into suspension with 30 cc of minoxidil. Any suitable concentration of minoxidil, including but not limited to 2%, 5%, etc., may be employed. However, it will be appreciated that between about 50 mg of Ostinol™ and about 450 g Ostinol™ may be mixed in suspension into between about 15 cc and 50 cc of liquid minoxidil. Also, it will be appreciated that any suitable shampoo or conditioner may be employed as a carrier.

In use, the composition is applied to the scalp of the human being treated. The composition may be applied at least once per day, preferably at least twice per day. However, it will be appreciated that the number of applications may vary based on the response. Additionally, it will be appreciated that the course of treatment may last as long as desired and/or needed.

While the present disclosure has been described in connection with what is considered the most practical and preferred embodiment, it is understood that this disclosure is not limited to the disclosed embodiments, but is intended to cover various arrangements included within the spirit and scope of the broadest interpretation so as to encompass all such modifications and equivalent arrangements.

What is claimed is:

1. A method for promoting hair growth in a human in need of promoting hair growth, consisting essentially of:
   preparing a suspension comprising:
      a composition comprising a partially hydrolyzed collagen and its associated proteins including Bone Morphogenetic Proteins, a Transforming Growth Factor Beta, an Insulin-like Growth Factor, a Platelet Derived Growth Factor, a Basic Fibroblastic Growth Factor, and a Vascular Endothelial Growth Factor; and
      minoxidil; and
   topically applying the suspension to the human.

2. The method of claim 1, wherein the Bone Morphogenetic Proteins comprise a percentage by weight of between about 35% and about 70% of the composition.

3. The method of claim 1, wherein the Transforming Growth Factor Beta comprises a percentage by weight of between about 2.5% and about 10% of the composition.

4. The method of claim 1, wherein the Insulin-like Growth Factor comprises a percentage by weight of between about 2.5% and about 10% of the composition.

5. The method of claim 1, wherein the Platelet Derived Growth Factor comprises a percentage by weight of between about 20% and about 40% of the composition.

6. The method of claim 1, wherein the Basic Fibroblastic Growth Factor comprises a percentage by weight of between about 2.5% and about 10% of the composition.

7. The method of claim 1, wherein the Vascular Endothelial Growth Factor comprises a percentage by weight of between about 2.5% and about 10% of the composition.

* * * * *